United States Patent [19]

Greindl et al.

[11] Patent Number: 5,733,342
[45] Date of Patent: Mar. 31, 1998

[54] HYDROXAMIC ACIDS AND HYDROXAMIC ACID ETHERS, AND THE USE THEREOF AS COMPLEXING AGENTS

[75] Inventors: Thomas Greindl, Neuburg; Alexander Kud, Eppelsheim; Volker Schwendemann, Neustadt; Michael Kneip, Frankenthal; Elisabeth Kappes, Mannheim; Richard Baur, Mutterstadt; Juergen Schneider, Freinsheim; Birgit Potthoff-Karl, Ludwigshafen; Alfred Oftring, Bad Durkheim, all of Germany

[73] Assignee: BASF Aktiengesellschaft, Ludwigshafen, Germany

[21] Appl. No.: 532,569

[22] PCT Filed: Apr. 15, 1994

[86] PCT No.: PCT/EP94/01166

§ 371 Date: Oct. 19, 1995

§ 102(e) Date: Oct. 19, 1995

[87] PCT Pub. No.: WO94/24096

PCT Pub. Date: Oct. 27, 1994

[30] Foreign Application Priority Data

Apr. 22, 1993 [DE] Germany .................. 43 13 137.9

[51] Int. Cl.$^6$ ............... C07C 259/06; C07C 259/08; C07C 259/10; C11D 3/39
[52] U.S. Cl. ............... 8/137; 560/171; 562/564; 562/437; 562/621; 134/2; 134/3; 134/41; 134/42; 510/109; 510/219; 510/234; 510/238; 510/239; 510/240; 510/241; 510/243; 510/244; 510/245; 510/246; 510/247; 510/252; 510/276; 510/361; 510/362; 510/531; 510/533
[58] Field of Search .................. 562/564, 437, 562/621; 560/171; 8/137, 107, 111; 510/109, 219, 234, 238, 239, 240, 241, 243, 244, 245, 246, 247, 252, 276, 361, 362, 533, 531; 134/2, 3, 41, 42

[56] References Cited

U.S. PATENT DOCUMENTS 4,232,112 11/1980 Kuse ...................... 430/393
4,822,886 4/1989 Donovan.
5,316,898 5/1994 Ueda et al. ............... 430/400

FOREIGN PATENT DOCUMENTS 458131   11/1991  European Pat. Off. .
0 563 571  2/1993  European Pat. Off. .
WO 91/08191  6/1991  WIPO .

OTHER PUBLICATIONS

Chemical Abstract No. 69:67681r, (month unknown), 1968.

Chemical Abstract No. 98:190619c, (month unknown), 1983.

Primary Examiner—Alan Diamond
Attorney, Agent, or Firm—Oblon, Spivak, McClelland, Maier & Neustadt, P.C.

[57] ABSTRACT

Hydroxamic acids and hydroxamic acid ethers I and II

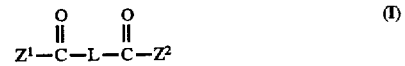

(I)

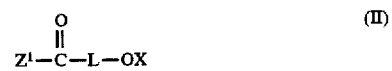

(II)

where $Z^1$ and $Z^2$ are —NH—OY, —NR$^1$—OY or —OX, where in the case of (I) at least one of $Z^1$ or $Z^2$, and in the case of (II) $Z^1$ is —NH—OY or —NR$^1$—OY, and $R^1$ is $C_1$–$C_{18}$-alkyl, X is hydrogen, alkali metal, ammonium or substituted ammonium, and Y is hydrogen, alkali metal, ammonium, substituted ammonium or $C_1$–$C_{18}$-alkyl, and L is a $C_1$–$C_{100}$ linker which can also carry oxygen and nitrogen functional groups, with the exception of N,N-bis(carboxymethyl)-2-aminoacetohydroxamic acid.

4 Claims, No Drawings

HYDROXAMIC ACIDS AND HYDROXAMIC ACID ETHERS, AND THE USE THEREOF AS COMPLEXING AGENTS

DISCUSSION OF THE BACKGROUND

1. Field of the Invention

This application is a 371 of PCT/EP94/01166 filed Apr. 15, 1994.

The present invention relates to hydroxamic acids and hydroxamic acid ethers of the general formula I and II

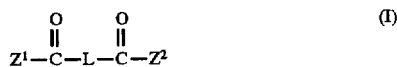

where $Z^1$ and $Z^2$ are —NH—OY, —NR$^1$—OY or —OX, where in the case of (I) at least one of $Z^1$ or $Z^2$, and in the case of (II) $Z^1$ is —NH—OY or —NR$^1$—OY, and $R^1$ is $C_1$–$C_{18}$-alkyl, X is hydrogen, alkali metal, ammonium or substituted ammonium, and Y is hydrogen, alkali metal, ammonium, substituted ammonium or $C_1$–$C_{18}$-alkyl, and L is a $C_1$–$C_{100}$ linker which can also carry oxygen and nitrogen functional groups, with the exception of N,N-bis(carboxymethyl)-2-aminoacetohydroxamic acid.

The invention furthermore relates to a process for preparing the compounds I and II, to the use thereof as complexing agents for alkaline earth metal and heavy metal ions, in particular as builder and as bleach stabilizers in detergents and cleaners, to detergents and cleaners containing compounds I and II, and to mixtures of compounds I and II with polycarboxylates.

2. Discussion of the Background

Complexing agents for alkaline earth metal ions and heavy metal ions, for example calcium, magnesium, manganese or copper, are required for a wide variety of industrial uses. Examples of relevant purposes and uses are: detergents and cleaners, industrial cleaners, electroplating, water treatment and polymerizations, the photographic industry, the textile industry and the papermaking industry, and various applications in pharmaceuticals, in cosmetics, in foodstuffs and in plant feeding.

Examples of complexing agents familiar to the skilled worker are nitrilotriacetic acid (NTA), ethylenediaminetetraacetic acid (EDTA), ethylenediaminetetramethylenephosphonic acid (EDTMP), propylenediaminetetraacetic acid (PDTA), hydroxypropylenediaminetetraacetic acid (HPDTA), isoserinediacetic acid (ISDA), β-alaninediacetic acid (β-ADA), hydroxyethanediphosphonic acid, diethylenetriaminetetraacetic acid, diethylenetriaminetetramethylenephosphonic acid, hydroxyethyleneaminodiacetic acid, hydroxyethylethylenediaminetriacetic acid, diethylenetriaminepentaacetic acid and, furthermore, diethanolglycine, ethanolglycine, citric acid, glucoheptonic acid or tartaric acid.

The effect of the known compounds, some of which are used, in large scale, is not always optimal in the individual case. For example, the effect of NTA as builder in detergents and cleaners to improve the white washing effect and to prevent deposits which cause encrustations and graying of the fabric is still in need of improvement. NTA also has only a weak effect as bleach stabilizer. Even EDTA, despite its good complexing capacity for heavy metals, shows only a moderate effect as bleach stabilizer in detergents and cleaners, and its effect as builder for improving the white washing effect is likewise in need of improvement.

In some cases, the biodegradability is also unsatisfactory. Thus, EDTA proves to have inadequate biodegradability in conventional tests, as does PDTA or HPDTA and corresponding aminomethylenephosphonates which, moreover, are often undesirable because of their phosphorus content.

EP-A 458 131 (1) recommends as Example 4 on page 11 the compound N,N-bis(carboxymethyl)-2-aminoacetohydroxamic acid as addition to photographic developing baths.

The later publication EP-A 563 571 (2) (named contracting states: DE, FR, GB and NL) discloses the hydroxamic acids of the formula

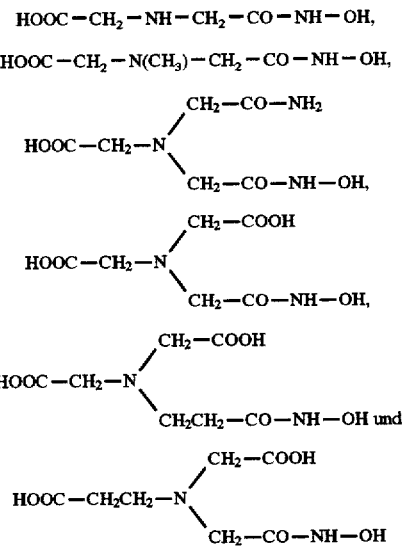

as bleaches for silver halide color photography. These compounds are used as iron complex.

U.S. Pat. No. 4,822,886 (3) describes cyclic N-hydroxyimide structures, which are prepared from citric esters and hydroxylamine in the presence of strong bases, as detergent additives.

SUMMARY OF THE INVENTION

It is an object of the present invention to provide novel complexing agents for alkaline earth metal and heavy metal ions for a wide variety of industrial uses, which, besides good complex-forming properties, in particular improved builder and bleach stabilizer properties in detergents and cleaners, are ecologically acceptable, where possible contain no phosphorus and can be satisfactorily degraded and eliminated biologically. The intention was also to develop a process for preparing these novel complexing agents which can be implemented industrially.

We have found that this object is achieved by the hydroxamic acids and hydroxamic acid ethers I and II defined at the outset.

DETAILED DESCRIPTION OF THE PREFERRED EMBODIMENTS

The compounds I and II according to the invention have the common structural feature that they contain at least two oxygen functional polar groups which act as complexing centers for alkaline earth metal and heavy metal ions. One of these two groups is always a hydroxamic acid functionality, which can be in etherified form; the other group is a carboxyl group which is in the free acid form or salt form, another hydroxamic acid (ether) functionality or a hydroxyl group. The complexing effect can be enhanced by other oxygen functional polar groups of the type mentioned, which are then part of the linker L.

The hydroxamic acid functionality in the compounds I and II can also be in an oxidized form (corresponding to the formula —CO—N=O).

The radical $R^1$ is linear or branched $C_1$–$C_{18}$-alkyl such as methyl, ethyl, n-propyl, isopropyl, n-butyl, isobutyl, sec-butyl, tert-butyl, n-amyl, isoamyl, tert-amyl, n-hexyl, n-heptyl, n-octyl, 2-ethylhexyl, n-nonyl, isononyl, n-decyl, n-undecyl, n-dodecyl, n-tridecyl, isotridecyl, n-tetradecyl, n-hexadecyl or n-octadecyl. $R^1$ is also a saturated or unsaturated long-chain fatty acid residue such as palmityl, stearyl, oleyl, linolyl or linolenyl. Preferred $R^1$ radicals are $C_1$–$C_8$-alkyl, in particular $C_1$–$C_4$-alkyl, radicals, especially methyl and ethyl.

Suitable for the variables X and Y besides hydrogen are alkali metal, eg. lithium, sodium or potassium, ammonium or substituted ammonium such as trialkylammoniumwith 1 to 4 carbon atoms in each alkyl radical, eg. trimethyl or triethylammonium, or trialkanolammonium with 2 or 3 carbon atoms in each alkanol residue, eg. triethanol-, tri-n-propanol- or triisopropanolammonium. If Y is $C_1$–$C_{18}$-alkyl, what has been said for $R^1$ similarly applies to these meanings.

The linker L contains 1 to 100 carbon atoms, preferably 2 to 40 carbon atoms, and is, in particular, the following:

methylene groups of the formula —$CR^9R^{10}$—;
1,2-ethylene groups of the formula —$CHR^9$—$CHR^{10}$—;
unsaturated 1,2-ethylene groups of the formula —$CR^9$=$CR^{10}$—;
where $R^9$ and $R^{10}$ are hydrogen, $C_1$–$C_{18}$-alkyl (for which what has been said about $R^1$ applies similarly), hydroxyl, or $C_1$–$C_4$-alkoxy (especially methoxy or ethoxy), and $R^9$ and $R^{10}$ can be linked together to form a saturated or unsaturated aliphatic or heterocyclic ring;
1,2-, 1,3- or 1,4-phenylene groups, where the aromatic nucleus can also carry further hydroxamic acid (ether) functionalities and/or carboxyl groups and/or hydroxyl groups;
groups of the formula

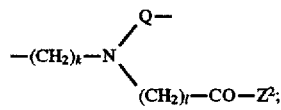

groups of the formula

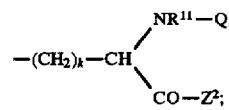

groups of the formula

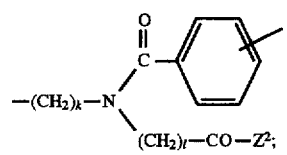

where k and l are each 1 to 20, in particular 1 to 8, especially 1 to 4, $R^{11}$ is hydrogen or a group of the formula —Q—CO—$Z^2$, Q is a $C_1$–$C_8$-alkylene group which can additionally carry up to 8 hydroxyl groups, and $Z^2$ is as defined above for —NH—OY, —$NR^1$—OY or —OX;

groups of the formula

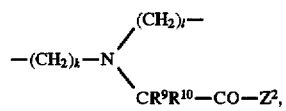

where k, l, $R^9$, $R^{10}$ and $Z^2$ have the abovementioned meanings;

groups of the formula

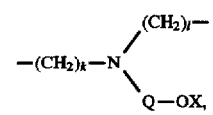

where k, l, Q and X have the abovementioned meanings;
epoxy groups of the formula

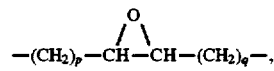

where p and q are each 0 to 10, in particular 0 to 4, especially 0 to 2;

groups of the formula —Q—, ie. a $C_1$–$C_8$-alkylene group, in particular a $C_1$–$C_4$-alkylene group, which can additionally carry up to 8, in particular up to 4, hydroxyl groups;

groups of the formula

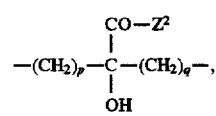

where p, q and $Z^2$ have the abovementioned meanings;
polyhydroxyalkylene groups, especially for compounds of type II, of the formula

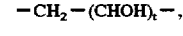

where t is from 2 to 8, in particular 3 to 6.

Typical examples of hydroxamic acids and hydroxamic acid ethers I and II are:

XOOC—$CH_2$—CO—NH—OH (N-hydroxymalonamic acid)

XOOC—$CH_2CH_2$—CO—NH—OH (N-hydroxysuccinamic acid)

HO—NH—CO—CH(OH)—$CH_2$—CO—NH—OH (malohydroxamic acid)

XOOC—$(CH_2)_3$—CO—NH—OH (N-hydroxyglutaramic acid)

XOOC—(CH₂)₄—CO—NH—OH (N-hydroxyadipamic acid)
XOOC—CH(OH)—CH(OH)—CO—NH—OH (N-hydroxytartaramic acid)
HO—NH—CO—CH(OH)—CH(OH)—CO—NH—OH (tartarohydroxamic acid)
2,4,5-tricarboxybenzohydroxamic acid
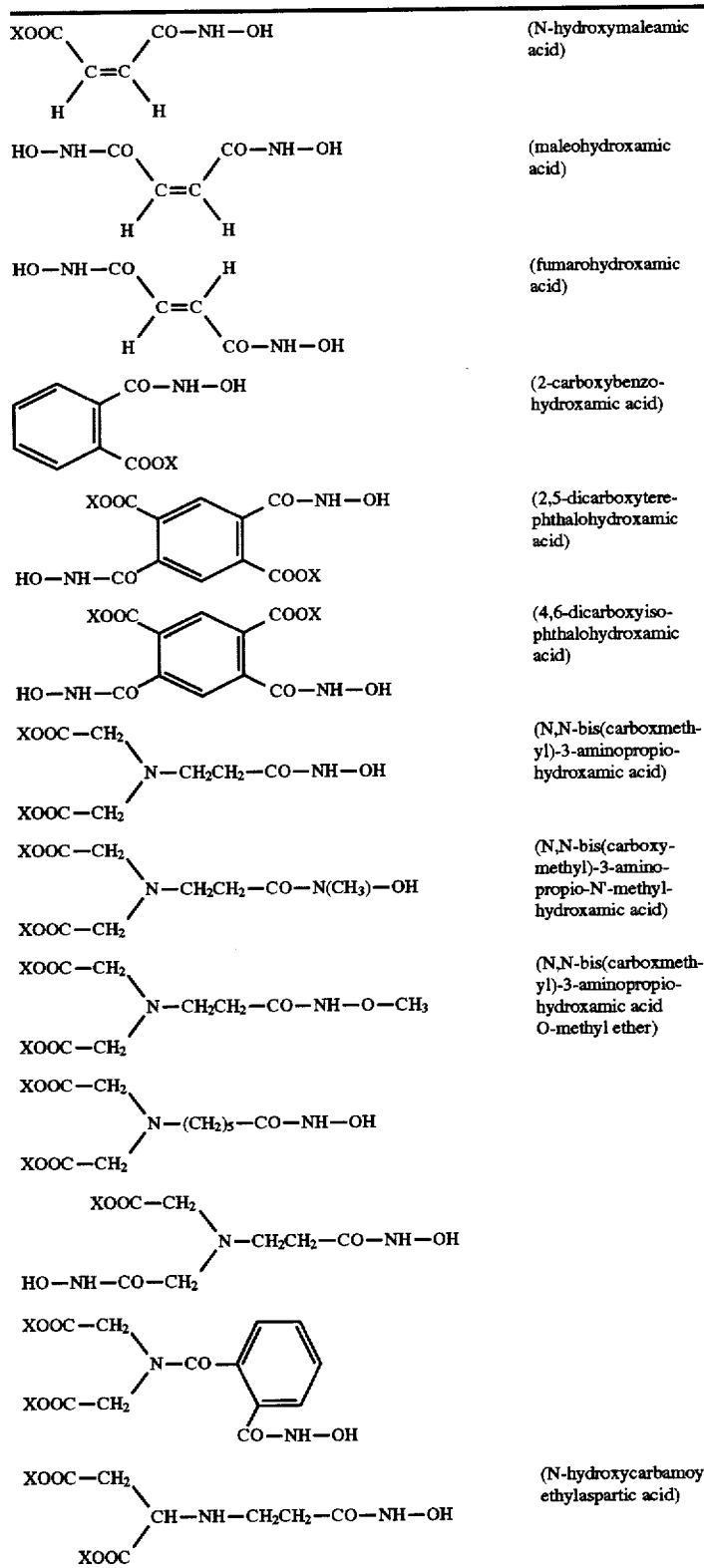

-continued

| | |
|---|---|
| XOOC—CH₂CH₂\<br>               CH—NH—CH₂CH₂—CO—NH—OH<br>XOOC/ | (N-hydroxycarbamoyl-<br>ethylglutamic acid) |
| XOOC—CH₂\<br>           N—CH₂—CH(OH)—CO—NH—OH<br>XOOC—CH₂/ | (N,N-bis(carboxy-<br>methyl)-3-amino-2-<br>hydroxypropio-<br>hydroxyamic acid) |
| XOOC—CH₂CH₂\<br>           N—CH₂—CO—NH—OH<br>XOOC—CH₂/ | (N-(2-hydroxyethyl)-<br>N-carboxymethyl-<br>aminoacetohydroxamic<br>acid) |
|                   O<br>                /  \<br>HO—NH—CO—CH——CH—CO—NH—OH | (epoxysuccino-<br>hydroxamic acid) |
|            OH<br>            |<br>XOOC—CH₂—C—CH₂—CO—NH—OH<br>            |<br>           COOX<br>           OH<br>           |<br>XOOC—CH₂—C—CH₂—COOX<br>           |<br>         CO—NH—OH | (monohydroxamic<br>acids of citric<br>acid) |
|                     OH<br>                    |<br>HO—NH—CO—CH₂—C—CH₂—CO—NH—OH<br>                    |<br>                  COOX<br>           OH<br>           |<br>XOOC—CH₂—C—CH₂—CO—NH—OH<br>           |<br>        CO—NH—OH | (dihydroxamic acids<br>of citric acid) |
|                     OH<br>                    |<br>HO—NH—CO—CH₂—C—CH₂—CO—NH—OH<br>                    |<br>                CO—NH—OH | (citrohydroxamic<br>acid) |
| HO—CH₂—(CHOH)₄—CO—NH—OH | (glucohydroxamic<br>acid) |
| HO—CH₂—(CHOH)₅—CO—NH—OH | (glucoheptono-<br>hydroxamic acid) |

Particularly preferred hydroxamic acids and hydroxamic acid ethers are those of the general formula III and IV

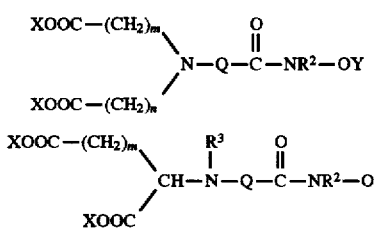

(III)

(IV)

where $R^2$ is hydrogen or $C_1$–$C_{18}$-alkyl, $R^3$ is hydrogen or a group of the formula —Q—CO—NR²—OY Q is a $C_1$–$C_8$-alkylene group, in particular $C_1$–$C_4$-alkylene group, which can additionally carry up to 8, in particular up to 4, hydroxyl groups, m and n are each 1 or 2, and X and Y have the abovementioned meanings.

Also particularly preferred are dihydroxamic acids and dihydroxamic acid ethers of the general formula V

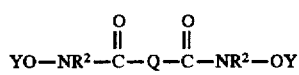

(V)

where $R^2$ is hydrogen or $C_1$–$C_{18}$-alkyl,

Q is a $C_1$–$C_8$-alkylene group, in particular $C_1$–$C_4$-alkylene group, which can additionally carry up to 8, in particular up to 4, hydroxyl groups, and Y has the abovementioned meanings.

N,N-Bis(carboxymethyl)-3-aminopropiohydroxamic acids and their ethers of the general formula IIIa

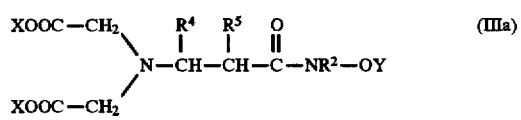

(IIIa)

where $R^4$ is hydrogen, methyl or ethyl, $R^5$ is hydrogen, methyl, ethyl or hydroxyl, and $R^2$, X and Y have the abovementioned meanings, are very particularly preferred.

The compounds IIIa are preferably in the form of free acids (X=Y=H), of monosodium or monopotassium salt at one carboxyl group (one X=Na or K, the other X=Y=H), of disodium or dipotassium salts at both carboxyl groups (X=Na or K, Y=H) or of trisodium or tripotassium salts (X=Y=Na or K).

The hydroxamic acids and their ethers I and II according to the invention and, of course, also their preferred subgroups III, IV, V and IIIa can expediently be prepared by reacting the underlying $C_1$-$C_4$-alkyl carboxylates or carboxamides, which may carry one or two $C_1$-$C_4$-alkyl groups on the amide nitrogen, with a hydroxylamine or a hydroxylamine $C_1$-$C_{18}$-alkyl ether, and converting the product if required into the salt form by treatment with the bases from which X and Y are derived.

The compounds IIIa can be prepared in an advantageous manner by reacting iminodiacetic acid of the formula VI

with an α,β-unsaturated carboxylic ester of the general formula VII

or with an α,β-unsaturated carboxamide of the general formula VIII

to give the N,N-bis(carboxymethyl)-3-aminopropionic ester of the general formula IX

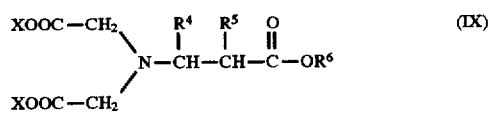

or the N,N-bis(carboxymethyl)-3-aminopropionamide of the general formula X

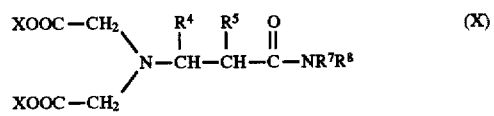

and subsequently reacting (IX) or (X) with a hydroxylamine or a hydroxylamine-$C_1$-$C_{18}$-alkyl ether to give the final product IIIa which can, if required, be converted into the salt form by treatment with the bases from which X and Y are derived, with the variables $R^4$, $R^5$, X and Y having the abovementioned meanings, and $R^6$ being $C_1$-$C_4$-alkyl, and $R^7$ and $R^8$ being hydrogen or $C_1$-$C_4$-alkyl.

Examples of suitable α,β-unsaturated carboxylic esters VII are the n-propyl-, isopropyl-, n-butyl-, isobutyl-, sec-butyl-, tert-butyl-, but especially the ethyl and very particularly preferably the methyl ester of acrylic acid, methacrylic acid, 2-ethylacrylic acid, crotonic acid, isocrotonic acid, 2-pentenoic acid, 2-methylcrotonic acid or 2-ethylcrotonic acid.

Examples of suitable α,β-unsaturated carboxamides VIII are the N-unsubstituted or N-mono- or N,N-dimethyl-substituted amides of said α,β-unsaturated acids.

Because handling is easier, hydroxylamine is preferably used in the form of one of its salts, such as hydroxylamine hydrochloride or hydroxylammonium sulfate, or as solution in an organic solvent, eg. ethanol or methanol.

Examples of suitable bases from which X and Y are derived are sodium hydroxide, sodium carbonate, potassium hydroxide, potassium carbonate, lithium hydroxide, ammonia, tri-$C_1$-$C_4$-alkylamines such as trimethyl- or triethylamine or tri-$C_2$-$C_3$-alkanolamines such as triethanol-, tri-n-propanol- or triisopropanolamine.

The two steps of addition of VI onto VII or VIII to give IX or X and reaction of IX or X with hydroxylamine can be carried out consecutively with or without isolation of the intermediate IX or X. Since the first step is expediently carried out in aqueous medium, if IX or X is isolated (two-stage variant), the subsequent reaction must be carried out in the absence of water in an organic solvent, eg. an alcohol such as methanol or ethanol, which in many cases leads to a somewhat purer product IIIa. On the other hand, the reaction VI to give IIIa can be completed without isolating IX or X (one-stage variant) in the same aqueous medium, which is more advantageous from the economic and ecological viewpoints (avoidance of organic solvents).

Water is particularly suitable as aqueous medium, but mixtures of water and water-miscible organic solvents such as methanol, ethanol, n-propanol, isopropanol, tert-butanol, dioxane or tetrahydrofuran are also suitable.

The reaction is expediently carried out in both steps at from 0° to 80° C., preferably from 10° to 60° C., under atmospheric pressure; however, elevated pressure can also be used.

The pH is, as a rule, from 4 to 10, preferably 5 to 9, in particular from 6 to 8. The procedure near to neutrality is particularly appropriate when the starting material is the monosalt of VI. Treatment with suitable bases or acids is necessary for conversion into the appropriate salt forms or the forms of the free acid of the intermediate IX or X or of the final product IIIa.

The reactants are preferably used in the stoichiometric or approximately stoichiometric ratio, ie. in a 1:1 molar ratio of VI: VII or VIII, with deviations of up to 5 % in the amounts of individual components still being tolerable. The preferred molar ratio of IX or X to hydroxylamine is likewise 1:1, but hydroxylamine can also be used in larger excess.

The compounds IIIa can be isolated in sufficiently pure form without difficulty. Particularly suitable for the free acid and the salts are spray- or freeze-drying, crystallization or precipitation. It may be advantageous for the resulting solution to be directly used industrially.

The present invention also relates to N,N-bis (carboxymethyl)-3-aminopropionic esters IX and N,N-bis (carboxymethyl)-3-amino-propionamides X as intermediates in the preparation of the N,N-bis(carboxymethyl)-3-aminopropiohydroxamic acids IIIa.

The hydroxamic acids and hydroxamic acid ethers I and II according to the invention are outstandingly suitable for complexing alkaline earth metal and heavy metal ions, especially calcium, magnesium, copper, iron and manganese ions. Because of this ability they have a large number of possible industrial uses. Since the compounds can be satisfactorily degraded and eliminated biologically, they can be used in large amounts wherever there is a need to treat waste water and avoid phosphorus-containing compounds.

The complexing agents according to the invention can be used in detergents and cleaners in order to control the content of free heavy metal ions in the detergents themselves and in the washing solutions. The amount used as complexing agent is expediently 0.1 to 2 % of the total weight of detergent ingredients.

They also have the advantageous effect of stabilizing bleaches, for example sodium perborate, in detergents and in the bleaching of textiles, pulp or paper raw materials. Traces of heavy metals such as iron, copper and manganese occur in the washing powder itself, in the water and in the textiles and catalyze the decomposition of sodium perborate. The complexing agents according to the invention bind these metal ions and prevent the unwanted decomposition of the bleaching system during storage and in the washing liquor. This increases the efficiency of the bleaching system and diminishes damage to fibers.

In addition, enzymes, optical brighteners and fragrances are protected from oxidative decomposition catalyzed by heavy metals.

The novel complexing agents can be used in liquid detergent formulations as preservatives, expediently in an amount of from 0.05 to 1% of the total weight of the detergent formulation.

In soaps, the novel complexing agents prevent, for example, oxidative decompostion catalyzed by metals.

They furthermore serve in an outstanding manner as builder in detergents and cleaners in order to prevent precipitations and incrustations on fabric.

They can advantageously be used in all industrial processes when precipitation of calcium, magnesium and heavy metal salts causes interference and is to be prevented. For example, to prevent deposits and incrustations in boilers, pipelines, on spray nozzles or generally on smooth surfaces.

They can be used to stabilize phosphates in alkaline degreasing baths and preventing precipitation of lime soaps and, in this way, prevent the tarnishing of non-ferrous surfaces and increase the useful lives of alkaline cleaning baths.

They can be used as complexing agents in alkaline rust removing and descaling baths, and in electroplating baths in place of cyanide in order to sequester impurities.

The treatment of cooling water with the novel complexing agents prevents deposits and dissolves those which are already present. An advantageous use is in alkaline media and thus elimination of corrosion problems.

They can be used in the preparation of the redox catalysts used in rubber polymerization. They additionally prevent the precipitation of iron hydroxide in the alkaline polymerization medium.

In the photographic industry, the novel complexing agents can be used in bleaching, fixing and bleach hardening baths prepared with hard water in order to prevent precipitation of calcium and magnesium salts of low solubility. The precipitates lead to gray fogging on films and images and to deposits in the tanks, which can thus advantageously be avoided. They can advantageously be used as iron(III) complexing solutions in bleach hardening baths, where they are able to replace the hexacyanoferrate solutions which are objectionable for ecological reasons.

In the textile industry, they can be used to remove traces of heavy metals during the manufacture and dyeing of natural and synthetic fibers. This prevents a large number of unwanted effects: spots and streaks on the textiles, loss of luster, poor wettability, unlevel dyeings and color faults.

In the papermaking industry, they can be used to eliminate heavy metals, especially manganese and iron ions. Deposition of iron on paper leads to "hot spots" at which catalytic oxidative decomposition of the cellulose starts.

The novel complexing agents can be used in industrial cleaner formulations for hard surfaces made of metal, plastic, paint or glass. Suitable uses for formulations of these types are alkaline rust removers, alkaline dip degreasers, all-purpose cleaners, detergents for brush and high-pressure car washes, steam jet cleaners, electrolytic degreasers, especially for steel, electrolytic rust removers, electrolytic descalers, highly alkaline cleaners, high-pressure cleaners, chain lubricants for conveyor belts for bottle filling and cleaning systems, passivating agents for steel, spray cleaners and aqueous low-temperature cleaners. It is, as a rule, possible to dispense with the presence of organic solvents in these cleaner formulations.

The novel complexing agents can be used in alkaline cleaner formulations which are essentially free of organic solvents for the drinks and foodstuffs industries, especially for bottle cleaning in the drinks industry and apparatus cleaning in dairies, in breweries, and in the production of conserves, of baked products and of sugar, and in the fat- and meat-processing industries.

The novel complexing agents can be used in dishwashing formulations, especially in phosphate-free compositions for mechanical dishwashing in domestic or commercial dishwashers, eg. in large kitchens or restaurants.

Examples of various suitable applications are in pharmaceuticals, cosmetics and foodstuffs, to prevent metal-catalyzed oxidation of olefinic double bonds and thus the products becoming rancid.

In plant feeding, copper, iron, manganese and zinc complexes of the novel complexing agents are used to eliminate heavy metal deficits. These heavy metals are added as chelates in order to prevent precipitation as biologically inactive insoluble salts.

Further applications of the novel complexing agents are in flue gas scrubbing, specifically to remove $NO_x$ from flue gases, in $H_2S$ oxidation, in metal extraction, and as catalysts for organic syntheses, eg. oxidation of paraffins with air or hydroformylation of olefins to alcohols.

The complexing agents according to the invention for alkaline earth metal and heavy metal ions are used as complexing agents in general and in particular in detergents and cleaners and in dishwashing compositions and laundry aids, as bleach stabilizers and as builders, but also in their function as pure complexing agents for said cations.

The invention accordingly also relates to the corresponding uses and detergents and cleaners which contain these compounds in addition to conventional ingredients known to the skilled worker. In particular, the present invention also relates to detergents and cleaners which, besides the compounds according to the invention, additionally contain a bleach system, ie. normally bleach or oxidizing agent and bleach activators, in the customary amount, because the activity of the compounds according to the invention is particularly effective in the presence of a bleach system of this type.

The compounds I according to the invention are used in detergent and cleaner formulations generally in an amount of from 0.01 to 50% by weight, preferably 0.02 to 40%, in particular 0.03 to 20%, especially 0.05 to 10%, of the total weight of the formulation.

Where used preferably as builder, amounts of from 1 to 10% by weight, and when used preferably as bleach stabilizer for perborates, amounts of from 0.05 to 1% by weight are particularly preferred. When used in particular as pure complexing agent in detergents, amounts of from 0.1 to 2% by weight are preferred.

The composition of detergent and cleaner formulations may vary widely. Detergents and cleaners normally contain from 2 to 50% by weight of surfactants with or without builders. These data apply both to liquid and to powdered detergents and cleaners. Examples of the composition of detergent formulations customary in Europe, the USA and Japan are to be found in tabulated form, for example, in Chemical and Engn. News 67 (1989) 35. Further details of the composition of detergents and cleaners can be found in WO-A 90 13581 and Ullmanns Encyclopädie der technischen Chemie, Verlag Chemie, Weinheim 1983, 4th Edition, pages 63–160. In addition, detergent formulations may contain up to 60% by weight of an alkali metal silicate and up to 10% by weight of a detergent polymer. Examples of suitable alkali metal silicates are the amorphous sodium disilicates which are describes in EP-A 0 444 415 and in DE-A 40 04 626, and crystalline sheet silicates which are present, as disclosed in EP-A 0 337 217, as builders in detergent formulations and are used, as disclosed in EP-B 0 164 514, for water softening, and sodium silicates which are obtainable by removing the water from sodium silicate solutions and drying to water contents of 15–23, preferably 18–20, % by weight.

Detergents may also, where appropriate, contain a bleach, eg. sodium perborate, which, if used, can be present in amounts of up to 30% by weight in the detergent formulation. The detergents and cleaners may, where appropriate, contain other conventional additives, eg. complexing agents, citrates, opacifying agents, optical brighteners, enzymes, perfume oils, color transfer inhibitors, antiredeposition agents and/or bleach activators.

Detergent and cleaner formulations which contain, based on the total weight, from 0.01 to 50, preferably from 0.02 to 40, in particular 0.03 to 20, especially 0.05 to 10, % by weight of the compounds according to the invention particularly contain as a rule as additional ingredients, based on the total weight, from 6 to 25% by weight of surfactants, 15 to 50% by weight of builders and, where appropriate, cobuilders, 5 to 35% by weight of bleaches and, where appropriate, bleach activators, 3 to 30% by weight of auxiliaries such as enzymes, foam regulators, corrosion inhibitors, optical brighteners, fragrances, dyes or formulation aids such as sodium sulfate.

The compounds according to the invention can be used in their property as complexing agents, builders and bleach stabilizers also in detergent and cleaner formulations together with other agents having the same function and known in the prior art, in which case the general properties in respect of sequestration, incrustation inhibition, antiredeposition action, single wash cycle performance and bleaching action may in some circumstances be distinctly improved by synergistic cooperation.

Synergism of this type occurs with mixtures of
A) hydroxamic acids or hydroxamic acid ethers of the general formula I or II and
B) polycarboxylates in the form of
  (i) homo-, co- or terpolymers of acrylic or methacrylic acid,
  (ii) homo-, co- or terpolymers of aspartic acid,
  (iii) homo-, co- or terpolymers of vinyl citrate or
  (iv) low molecular weight mono- to hexacarboxylic acids
as free acids or as alkali metal, ammonium or substituted ammonium salts,
in the A:B ratio by weight of from 50:1 to 1:20, preferably 20:1 to 1:15.

Particularly preferred in this connection are mixtures of
A) N,N-bis(carboxymethyl)-3-aminopropiohydroxamic acids or their ethers of the general formula IIIa and
B) alkali metal salts of citric acid
in the A:B ratio by weight of from 20:1 to 1:20, in particular 10:1 to 1:10.

The present invention therefore also relates to mixtures of these types.

Said polycarboxylates mean, in particular:
(i) Homo-, co- and terpolymers of acrylic acid (methacrylic acid). Cocomponents which may be suitable are unsaturated mono- and dicarboxylic acids (eg. crotonic acid, maleic acid, itaconic acid) and water-insoluble vinyl compounds (eg. vinyl acetate). The Fikentscher K value (1% by weight in water as Na salt) of these compounds is, as a rule, from 5 to 100.
(ii) Homo-, co- and terpolymers of aspartic acid. Cocomponents which may be suitable are mono-, di- and polyfunctional low molecular weight and high molecular weight carboxylic acids (or anhydrides) or their salts (Na, K, ammonium, tert. amine) and water-insoluble vinyl compounds (eg. vinyl acetate). The Fikentscher K value (1% by weight in water as Na salt) of these compounds is, as a rule, from 5 to 100.
(iii) Homo-, co- and termpolymers of vinyl citrate. Cocomponents which may be suitable are mono-, di- and polyfunctional, low molecular weight and high molecular weight carboxylic acids (or anhydrides) or their salts (Na, K, ammonium, tert. amine) and water-insoluble vinyl compounds (eg. vinyl acetate). The Fikentscher K value (1% by weight in water as Na salt) of these compounds is, as a rule, from 5 to 100.
(iv) Low molecular weight mono-, di-, tri-, tetra-, penta- and hexacarboxylic acids or their salts. The basic skeleton can be aliphatic or aromatic in nature. Examples are phthalic acid, terephthalic acid, benzenehexa(or tetra)carboxylic acid, citric acid, malic acid.

Conventional ingredients known to the skilled worker for detergent formulations based on the outline indicated above may be listed by way of example below:

Suitable surfactants are those which contain in the molecule at least one hydrophobic organic radical and an anionic, zwitterionic or nonionic group which makes it soluble in water. The hydrophobic radical is usually an aliphatic hydrocarbon radical with 8 to 26, preferably 10 to 22 and, in particular, 12 to 18 carbon atoms, or an alkylaromatic radical with 6 to 18, preferably 8 to 16, aliphatic carbon atoms.

Suitable synthetic anionic surfactants are, in particular, those of the sulfonate, sulfate or synthetic carboxylate types.

Suitable surfactants of the sulfonate type are alkylbenzenesulfonates with 4 to 15 carbon atoms in the alkyl, mixtures of alkene- and hydroxyalkanesulfonates, and disulfonates as obtained, for example, from monoolefins with terminal or non-terminal double bond by sulfonation with gaseous sulfur trioxide and subsequent alkaline or acidic hydrolysis of the sulfonation products. Also suitable are alkanesulfonates which are obtainable from alkanes by sulfochlorination or sulfoxidation and subsequent hydrolysis or neutralization or by bisulfite addition onto olefins. Further surfactants of the sulfonate type which can be used are the esters of α-sulfo fatty acids, eg. the α-sulfo fatty acids from hydrogenated methyl or ethyl esters of coconut, palm kernel or tallow fatty acid.

Suitable surfactants of the sulfate type are the sulfuric monoesters of primary alcohols, eg. of coconut fatty alcohols, tallow fatty alcohols or oleyl alcohol, and those of secondary alcohols. Also suitable are sulfated fatty acid alkanolamines, fatty acid monoglycerides or the products of the reaction of 1 to 4 mol of ethylene oxide with primary or secondary fatty alcohols or alkylphenols.

Other suitable anionic surfactants are the fatty acid esters or amides of hydroxy or amino carboxylic acids or sulfonic acids, such as the fatty acid sarcosides, glycolates, lactates, taurides or isethionates.

The anionic surfactants may be present in the form of their sodium, potassium and ammonium salts and as soluble salts of organic bases such as mono-, di- or triethanolamine. Conventional soaps, ie. salts of natural fatty acids, should not be left unmentioned.

Nonionic surfactants (nonionics) which can be used are, for example, adducts of 3 to 40, preferably 4 to 20, mol of ethylene oxide and 1 mol of fatty alcohol, alkylphenol, fatty acid, fatty amine, fatty acid amide or alkanesulfonamide. The adducts of 5 to 16 mol of ethylene oxide and coconut or tallow fatty alcohols, oleyl alcohol or synthetic alcohols with 8 to 18, preferably 12 to 18, carbon atoms, and mono- or dialkylphenols with 6 to 14 carbon atoms in the alkyl radicals, are particularly important. However, besides these water-soluble nonionics, also of interest are polyglycol ethers with 1 to 4 ethylene glycol ether residues in the molecule which are insoluble or incompletely soluble in water especially when they are used together with water-soluble nonionic or anionic surfactants.

It is also possible to use as nonionic surfactants the water-soluble adducts, which contain 20 to 250 ethylene glycol ether groups and 10 to 100 propylene glycol ether groups, of ethylene oxide and polypropylene glycol ethers, alkylenediaminopolypropylene glycol and alkylpolypropylene glycols with 1 to 10 carbon atoms in the alkyl chain, in which the polypropylene glycol ether chain acts as hydrophobic radical.

Nonionic surfactants of the amine oxide or sulfoxide types can also be used.

The foaming capacity of the surfactants can be increased or reduced by combining suitable types of surfactants. A reduction can also be achieved by adding non-surfactant organic substances.

Examples of suitable builder substances are: washing alkalis such as sodium carbonate and sodium silicate or complexing agents such as phosphates or ion exchangers such as zeolites, and mixtures thereof. These builders have the task of eliminating the hardness ions which originate partly from the water and partly from the soil or the textiles, and assisting the surfactant action. Besides said builder substances, it is possible for the builders to contain cobuilders. Cobuilders have the task in modern detergents of taking over some of the properties of the phosphates, such as sequestration, soil antiredeposition power, and single and multiwash cycle performance.

The builder may contain, for example, water-insoluble silicates as described, for example, in DE-A 24 12 837, and/or phosphates. Phosphates which can be used are pyrophosphate, triphosphate, higher polyphosphates and metaphosphates. Further suitable detergent ingredients are phosphorus-containing organic complexing agents such as alkanepolyphosphonic acids, amino- and hydroxyalkanepolyphosphonic acids and phosphono carboxylic acids. Examples of such detergent additives are the following compounds: methanedisulfonic acid, propane-1,2,3-triphosphonic acid, butane-1,2,3,4-tetraphosphonic acid, polyvinylphosphonic acid, 1-aminoethane-1,1-diphosphonic acid, 1-amino-1-phenyl-1,1-diphosphonic acid, aminotrimethylenetriphosphonic acid, methylamino- or ethylaminodimethylenediphosphonic acid, ethylenediaminetetramethylenetetraphosphonic acid, diethylenetriaminepentamethylenepentaphosphonic acid, 1-hydroxyethane-1,1-diphosphonic acid, phosphonoacetic and phosphonopropionic acids, copolymers of vinylphosphonic acid and acrylic and/or maleic acid and the partially or completely neutralized salts thereof.

Other organic compounds which act as complexing agents for calcium and may be present in detergent formulations are polycarboxylic acids, hydroxy carboxylic acids and amino carboxylic acids, which are usually employed in the form of their water-soluble salts.

Examples of polycarboxylic acids are dicarboxylic acids of the general formula HOOC—(CH$_2$)m—COOH with m=0 to 8, in addition maleic acid, methylenemalonic acid, citraconic acid, mesaconic acid, itaconic acid, acyclic polycarboxylic acids with at least 3 carboxyl groups in the molecule, eg. tricarballylic acid, aconitsic acid, ethylenetetracarboxylic acid, 1,1,3-propanetetracarboxylic acid, 1,1,3,3,5,5-pentanehexacarboxylic acid. Hexanehexacarboxylic acid, cyclic di- or polycarboxylic acids, such as cyclopentanetetracarboxylic acid, cyclohexanehexacarboxylic acid, tetrahydrofurantetracarboxylic acid, phthalic acid, terephthalic acid, benzenetri-, -tetra- or -pentacarboxylic acid and mellitic acid.

Examples of hydroxy-mono- or polycarboxylic acids are glycolic acid, lactic acid, malic acid, tartronic acid, methyltartronic acid, gluconic acid, glyceric acid, citric acid tartaric acid or salicylic acid.

Examples of amino carboxylic acids are glycine, glycylglycine, alanine, asparagine, glutamic acid, aminobenzoic acid, iminodi- or -triacetic acid, hydroxyethyliminodiacetic acid, ethylenediaminetetraacetic acid, hydroxyethylethylenediamine-triacetic acid, diethylenetriaminepentaacetic acid and higher homologs which can be prepared by polymerization of an N-azidirylcarboxylic acid derivate, eg. of acetic acid, succinic acid, tricarballylic acid and subsequent hydrolysis, or by condensation of polyamines with a molecular weight of from 500 to 10,000 with salts of chloroacetic acid or bromoacetic acid.

Polymeric carboxylic acids are preferably used as cobuilder substances. These polymeric carboxylic acids also include the carboxymethyl ethers of sugars, of starch and of cellulose.

Particularly important polymeric carboxylic acids are, for example, the polymers of acrylic acid, maleic acid, itaconic acid, mesaconic acid, aconitic acid, methylenemalonic acid and citraconic acid, the copolymers of the abovementioned carboxylic acids with one another, eg. a copolymer of acrylic acid and maleic acid in ratio 70:30 of molecular weight 70,000, or with ethylenically unsaturated compounds such as ethylene, propylene, isobutylene, vinyl alcohol, vinyl methyl ether, furan, acrolein, vinyl acetate, acrylamide, acrylonitrile, methacrylic acid or crotonic acid, eg. the 1:1 copolymers of maleic anhydride and methyl vinyl ether of molecular weight 70,000 or the copolymers of maleic anhydride and ethylene or propylene or furan.

The cobuilders may additionally contain soil carriers which keep the soil which has been detached from the fibers suspended in the liquor and thus inhibiting redeposition. Suitable for this purpose are water-soluble colloids, which are usually organic in nature, such as the water-soluble salts of polymeric carboxylic acids, glue, gelatin, salts of ether carboxylic acids or ether sulfonic acids of starch or of cellulose or of salts of acidic sulfuric esters of cellulose or of starch. Water-soluble polyamides containing acidic groups are also suitable for this purpose. It is also possible to use starch products which are soluble and differ from those mentioned above, eg. degraded starch or aldehyde starches; polyvinylpyrrolidone can also be used for this purpose.

Bleaches are, in particular, hydrogen peroxide and derivatives thereof or compounds providing active chlorine. Among the compounds acting as bleaches and providing H2O2 in water, sodium perboratehydrates such as NaBO$_2$.H$_2$O$_2$.3H$_2$O and NaBO$_2$.H$_2$O$_2$ have particular importance. However, other borates which provide $H_2O_2$ can also be used. These compounds may be partly or completely replaced by other active oxygen donors, especially by peroxyhydrates, such as peroxycarbonates, peroxyphosphates, citrate perhydrates, urea-$H_2O_2$ or melamine-$H_2O_2$ compounds, and salts of peracids providing $H_2O_2$, such as caroates, perbenzoates or peroxyphthalates.

It is possible to incorporate conventional water-soluble and/or water-insoluble stabilizers, besides those according to the invention, for the peroxy compounds in amounts of from 0.25 to 10% of the weight of the peroxy compounds. Suitable water-insoluble stabilizers are the magnesium silicates which are usually obtained by precipitation from aqueous solutions and have a composition (MgO:SiO$_2$) of from 4:1 to 1:4, preferably 2:1 to 1:2 and, in particular, 1:1. However alkaline earth metal silicates of corresponding composition can also be used in their place.

In order to obtain a satisfactory bleaching effect when washing at temperatures below 80° C., in particular in the range from 40° to 60° C., it is expedient to incorporate bleach activators into the detergents, advantageously in an amount of from 5 to 30% of the weight of the compound providing $H_2O_2$.

Activators used for peroxy compounds which provide $H_2O_2$ in water are certain N-acyl or O-acyl compounds which form organic peracids with $H_2O_2$, in particular acetyl, propionyl or benzoyl compounds, and carbonic and pyrocarbonic esters. Compounds which can be used include:

suger esters, eg. pentaacetylglucose;

acyloxybenzenesulfonic acids and their alkali metal and alkaline earth metal salts, eg. sodium p-isononanoyloxybenzenesulfonate or sodium p-benzoyloxybenzenesulfonate;

N-diacylated and N,N'-tetraacylated amines, eg. N,N,N', N'-tetraacetylmethylenediamine and -ethylenediamine, N,N-diacetylaniline, N,N-diacetyl-p-toluidine or 1,3-diacylated hydantoins such as 1,3-diacetyl-5,5-dimethylhydantoin;

(4H)1,3-benzoxazin-4-ones, eg. 2-phenyl-(4H)1,3-benzoxazin-4-one or 2-methyl-(4H)l,3-benzoxazin-4-one;

N-alkyl-N-sulfonylcarboxamides, eg. N-methyl-N-mesylacetamide or N-methyl-N-mesylbenzamide;

N-acylated cyclic hydrazides, acylated triazoles or urazoles, eg. the monoacetyl derivative of maleic hydrazide;

O,N,N-trisubstituted hydroxylamines, eg. O-benzoyl-N,N-succinythydroxylamine, O-acetyl-N,N-succinylhydroxylamine or O,N,N-triacetylhydroxylamine;

N,N'-diacylsulfamides, eg. N,N'-dimethyl-N,N'-diacetylsulfamide or N,N'-diethyl-N,N'-dipropionylsulfamide;

triacyl cyanurates, eg. triacetyl cyanurate or tribenzoyl cyanurate;

carboxylic anhydrides, eg. benzoic anhydride, m-chlorobenzoic anhydride or phthalic anhydride;

1,3-diacyl-4,5-diacyloxyimidazoles, eg. 1,3-diacetyl-4,5-diacetoxyimidazoline;

tetraacetylglycoluril and tetrapropionylglycoluril;

diacylated 2,5-diketopiperazines, eg. 1,4-diacetyl-2,5-diketopiperazine;

products of the acylation of propylenediurea and 2,2-dimethylpropylenediurea, eg. tetraacetylpropylenediurea;

α-acyloxypolyacylmalonamides, eg. α-acetoxy-N,N'-diacetylmalonamide;

diacyldioxohexahydro-1,3,5-triazines, eg. 1,5-diacetyl-2,4-dioxohexahydro-1,3,5-triazine.

It is also possible to use active chlorine compounds which are inorganic or organic in nature as bleaches. Inorganic active chlorine compounds include alkali metal hypochlorites, which can be used, in particular, in the form of their mixed salts or adducts with orthophosphates or condensed phosphates such as pyro- and polyphosphates, or with alkali metal silicates. If the detergents and detergent auxiliaries contain monopersulfates and chlorides, active chlorine is produced in aqueous solution.

Particularly suitable organic active chlorine compounds are the N-chloro compounds in which one or two chlorine atoms are bonded to a nitrogen atom, with the third valency of the nitrogen atoms preferably leading to a negative group, in particular to a CO or SO$_2$ group. These compounds include dichloro- and trichlorocyanuric acid and salts thereof, chlorinated alkylguanides or alkylbiguanides, chlorinated hydantoins and chlorinated melamines.

Suitable foam regulators are, especially when surfactants of the sulfonate or sulfate type are used, carboxy- or sulfobetaines with capillary activity, and the abovementioned nonionics of the alkylolamide type. Fatty alcohols or higher terminal diols are also suitable for this purpose.

A reduced foaming capacity, which is particularly required for machine washing, is often achieved by combining various types of surfactants, eg. sulfates and/or sulfonates with nonionics and/or with soaps. In the case of soaps, the foam reduction increases with the degree of saturation and the carbon number of the fatty acid ester; soaps of saturated $C_{20}$–$C_{24}$ fatty acids are therefore particularly suitable as foam inhibitors.

Non-surfactant foam inhibitors include where appropriate chlorine-containing N-alkylated aminotriazines which are obtained by reacting 1 mol of cyanuric chloride with 2 to 3 mol of a mono- and/or dialkylamine with 6 to 20, preferably 8 to 18, carbon atoms in the alkyl radical. Propoxylated and/or butoxylated aminotriazines have a similar effect, eg. products obtained by addition of 5 to 10 mol of propylene oxide onto 1 mol of melamine and further addition of 10 to 50 mol of butylene oxide onto this propylene oxide derivative.

Also suitable as non-surfactant foam inhibitors are water-insoluble organic compounds such as paraffins or haloparaffins with melting points below 100° C., aliphatic $C_{18}$–$C_{40}$ketones and aliphatic carboxylic esters which contain at least 18 carbon atoms in the acid residue or alcohol residue, where appropriate also in each of these two residues, eg. triglycerides or fatty acid fatty alcohol esters; they can be used especially in combinations of surfactants of the sulfate and/or sulfonate type with soaps for inhibiting foam.

The detergents can contain optical brighteners for cotton, for polyamide, polyacrylonitrile or polyester fabric. Examples of suitable optical brighteners are derivatives of diaminostilbenedisulfonic acid for cotton, derivatives of 1,3-diarylpyrazolines for polyamide, quaternary salts of 7-methoxy-2-benzimidazol-2-ylbenzofuran or derivatives from the class of 7-(1,2,5-triazol-1-yl)-3-(1,2,4-triazol-1-yl) coumarins for polyacrylonitrile. Examples of brighteners suitable for polyesters are products from the class of substituted styrils, ethylenes, thiophenes, naphthalenedicarboxylic acids or derivatives thereof, stilbenes, coumarins and naphthalimides.

Further auxiliaries or formulation aids which can be used are the substances known to the skilled worker, eg. solubilizers such as xylene- or cumenesulfonates, fillers such as sodium sulfate, enzymes or perfume oils.

The detergents and cleaners according to the invention can be in powder or liquid form.

PREPARATION EXAMPLES

Example 1
Synthesis of N,N-bis(carboxymethyl)-3-aminopropiohydroxamic acid monosodium salt (one-stage variant)

66.5 g (0.50 mol) of iminodiacetic acid were dissolved in 200 ml of water and adjusted to pH 8 with 40.0 g (0.50 mol) of 50 % by weight aqueous NaOH. Then, over the course of 30 min, 43.0 g (0.50 mol) of methyl acrylate were added dropwise to this solution at 20° C. The solution was then stirred at 20° C. for 12 h and, after this time, the degree of conversion according to HPLC was 95%. Subsequently, 34.3 g (0.50 mol) of hydroxylamine hydrochloride were added, and the mixture was stirred at 20° C. for a further 3 h, keeping the pH constant at 7 by adding a total of 40.0 g (0.50 mol) of 50% by weight aqueous NaOH. After this time, the intermediate methyl N,N-bis(carboxymethyl)-3-aminopropionate had completely reacted, and only the title compound was then detectable as final product; the calcium complexing capacity corresponded to 94% of theory. Addition of 650 ml of methanol caused the title compound to precipitate as hygroscopic oil in a yield of 106 g (corresponding to 97% of theory).

Example 2
Synthesis of N,N-bis(caroboxymethyl)-3-aminopropiohydroxumic acid disodium salt (two-stage variant)

Example 2
Preparation of methyl N,N-bis(carboxymethyl)-3-aminopropionate 133 g (1.00 mol) of iminodiacetic acid were dissolved in 530 ml of water, and the solution was adjusted to pH 7.0 with 40.5 g (1.00 mol) of solid NaOH. 86.0 g (1.00 mol) of methyl acrylate were added dropwise to this solution at 20° C., and the mixture was then stirred for 6 h. The methyl acrylate content after this time had fallen to 0.6% of the initial amount, and the pH was adjusted to 2 by adding 98.5 ml of concentrated HCl. Methyl N,N-bis(carboxymethyl)-3-aminopropionate separated out as colorless precipitate overnight at 5° C. Filtering off and drying resulted in 210 g (corresponding to a yield of 96% of theory) of a pure product of melting point 141° C.

Example 2b
Conversion to N,N-bis(carboxymethyl)-3-aminopropiohydroxamic acid disodium salt 51.5 g (0.235 mol) of the ester of Example 2a were suspended in 50 ml of methanol, and 600 g (1.26 mol) of a 6.9% by weight methanolic solution of hydroxylamine were added dropwise to this suspension at 20° C. The reaction mixture was then stirred at 20° C. for 25 h and subsequently distilled to remove volatile constituents. The remaining resinous product was highly hygroscopic and was therefore dissolved in 130 ml of water and, after addition of 94.0 g (0.470 mol) of 20% by weight aqueous NaOH, again freed of solvent and dried under reduced pressure. The colorless powder was obtained pure by reprecipitation twice from a methanol/water/acetone mixture. 58.5 g (corresponding to a yield of 92% of theory) of the title compound resulted.

Example 3
N,N-Bis(carboxymethyl)-3-aminopropio-N-methylhydroxamic acid disodium salt from iminodiacetic acid 36.8 g of 50% by weight aqueous sodium hydroxide solution and 19.8 g of methyl acrylate were successively added to a suspension of 30.6 g of iminodiacetic acid in 95 g of water at 15° C. After 45 min at 15° C., 19.8 g of N-methylhydroxylammonium chloride dissolved in 50 g of water were added dropwise to the solution and, at the same time, the pH was kept at 9.8 by adding a total of 17.8 g of 50% by weight aqueous sodium hydroxide solution. After 30 h at 20° C., the ester conversion was 99%, and freeze drying resulted in 80.0 g of product containing 57% N,N-bis(carboxymethyl)-3-aminopropio-N-methylhyroxamic acid disodium salt (yield corresponding to 71% of theory), 7.5% water, 16% sodium chloride and 19% β-alanine-N,N-diacetic acid disodium salt.

Example 4
N,N-Bis(carboxymethyl)-3-aminopropiohydroxamic acid O-methyl ether disodium salt from methyl N,N-bis(carboxymethyl)-3-aminopropionate 16.0 g of 50% by weight aqueous sodium hydroxide solution and 8.6 g of methyl acrylate were successively added to a suspension of 13.3 g of iminodiacetic acid in 41.5 g of water at 15° C. After 60 min at 10° C., 8.3 g of methoxylamine hydrochloride were added to the solution and, at the same time, the pH was kept at 10.0 by adding a total of 8.4 g of 50% by weight sodium hydroxide solution. After 30 h at 20° C., the ester conversion was 99% of theory, and freeze drying resulted in 31.1 g of product containing 68% N,N-bis(carboxymethyl)-3-aminopropiohydroxamic acid O-methyl ether disodium salt and with a calcium binding capacity of 2.435 mmol/g (yield corresponding to 77% of theory), and containing 5.6% water, 19% sodium chloride.

Example 5
N-Hydroxycarbamoyl-D,L-aspartic acid from D,L-aspartic acid 80 g of 50% by weight aqueous sodium hydroxide solution and 43.0 g of methyl acrylate were successively added dropwise to a suspension of 66.5 g of aspartic acid in 207 g of water at 10° C. After 4 h at 10° C., 99% of theory of the methyl acrylate had reacted, and 33.0 g of hydroxylammonium chloride dissolved in 50 g of water were added dropwise. During this, the pH was kept at 11 by adding a total of 38.6 g of 50% by weight aqueous sodium hydroxide solution. After 30 h at room temperature, the pH was reduced to 2 by adding 34 g of 37% by weight aqueous hydrogen chloride, and concentration by distilling out water resulted in 340 g of a solution of 28% D,L-aspartic acid N-propiohydroxamic acid (corresponding to 92.5% of the theoretical yield).

Example 6
N,N-Bis(carboxymethyl)-3-aminopropiohydroxamic acid disodium salt from iminodiacetic acid and acrylamide 16.8 g of 50% by weight aqueous sodium hydroxide solution and 7.4 g of acrylamide were successively added to a suspension of 13.8 g of iminodiacetic acid in 60 g of water, and the mixture was stirred at room temperature for 4 h. Then, 6.3 g of hydroxylammonium chloride were added to the resulting solution of 26% by weight N,N-bis (carboxymethyl)-propionamide disodium salt and, at the same time, the pH was kept at 10 by adding a total of 6.8 g of 50% by weight aqueous sodium hydroxide solution. After 21 h at 20° C., a solution of 20.8% N,N-bis(carboxymethyl)-3-aminopropiohydroxamic acid disodium salt with an iron binding capacity of 0.788 mmol/g (corresponding to a yield of 97% of theory) was obtained.

Example 7
N,N-Bis(carboxymethyl)-3-amino-2-hydroxypropiohydroxamic acid disodium salt from N,N-bis(carboxymethyl)-3-amino-2-hydroxypropionamide disodium salt 3.4 g of 50% by weight aqueous sodium hydroxide solution and 6.3 g of hydroxylammonium chloride were successively added to a 17% by weight aqueous solution of 142 g of N,N-bis(carboxymethyl)-3-amino-2-hydroxypropionamide disodium salt. During this, the pH was kept at 10 by adding a total of 7.8 g of 50% by weight aqueous sodium hydroxide solution. After 30 h at 40° C., 159 g of a solution of 11.8% N,N-bis(carboxymethyl)-3-amino-2-hydroxypropiohydroxamic acid disodium salt with an iron binding capacity of 0.458 mmol/g (corresponding to a yield of 73% of theory) were obtained.

Example 8
Epoxysuccinohydroxamic acid

At room temperature, 25.5 g of dimethyl epoxysuccinate were dissolved in 1100 g of a 1.35% by weight solution of hydroxylamine in anhydrous ethanol, and the mixture was left to stand at room temperature for 3 h. During this, a precipitate of 25.3 g of epoxysuccinohydroxamic acid with an iron binding capacity of 3.6 mmol/g (corresponding to 61% of the theoretical yield) formed. A pure product was obtained by reprecipitation from ethanol.

Example 9
2,5-Dicarboxyterephthalohydroxamic acid, 4,6-dicarboxyisophthalohydroxamid acid 47.9 g of 50% by weight aqueous sodium hydroxide solution were added to a mixture of 49.2 g of hydroxylammonium sulfate in 100 g of water and 50 g of 1-propanol. Then, 65.4 g of benzenetetracarboxylic dianhydride were added to this mixture at 10° C. and, at the same time, the pH was kept at from 8 to 9 with a total of 54.2 g of 50% by weight aqueous sodium hydroxide solution. The mixture was kept at 0° to 10° C. for 1 h and then adjusted to pH 3.0 with 7.8 g of sulfuric acid (96% by weight), resulting in a precipitate of a mixture of 2,5-dicarboxyterephthalohydroxamic acid and 2,4-dicarboxyisophthalohydroxamic acid in a yield of 86% of theory.

Example 10
Tartarohydroxamic acid 25.6 g of a 6.45% by weight solution of hydroxylamine in ethanol were added dropwise to a solution of 10.5 g of diethyl tartarate in 15 g of ethanol at 0° to 15° C. After stirring at room temperature for 4 h, 15 g of water were added, and the reaction was continued at 50° C. for 2 h, keeping the pH at 9 by adding 7.7 g of a 50% by weight solution of NaOH. After cooling, two phases formed, and the lower oily phase formed 10.6 g of a mixture of tartarohydroxamic acid and diethyl tartrate. Pure tartarohydroxamic acid was obtained (in a yield of 83%) by extracting the mixture with ethanol.

It was also possible to convert diethyl malate, succinate, maleate and fumarate into bishydroxamic acids as in Example 10.

Example 11
Citrohydroxamic acid 178 g of a 9.24% by weight solution of hydroxylamine in methanol were added dropwise to a solution of 27.6 g of triethyl citrate in 100 g of methanol at 20° C. After 4 h at room temperature, a colorless precipitate formed and was filtered off and washed with methanol. Drying at 50° C. resulted in 13.7 g of citrohydroxamic acid (corresponding to 58% of the theoretical yield) with an iron binding capacity of 5.01 mmol/g.

It was also possible by the same process to prepare the monohydroxamic and bishydroxamic acids of citric acid by adding appropriate equivalents of hydroxylamine and subsequently hydrolyzing.

Example 12
D-Gluconohydroxamic acid 25.6 g of a 6.44% by weight solution of hydroxylamine in ethanol were added dropwise to a solution of 8.9 g of D-gluconolactone in 24.0 g of water at room temperature. After 24 h at room temperature, removal of the volatile constituents by distillation under reduced pressure resulted in 10.3 g of D-gluconohydroxamic acid which was purified by reprecipitation from ethanol to afford 86% of the theoretical yield.

Example 13
D-Glucoheptonohydroxamic acid 25.6 g of a 6.44% by weight solution of hydroxylamine in ethanol were added dropwise to a solution of 10.4 g of D-glucoheptonolactone in 30.3 g of water at room temperature. After 24 h at room temperature, removal of the volatile constituents by distillation under reduced pressure resulted in 11.9 g of D-glucoheptonohydroxamic acid which was purified by reprecipitation from ethanol to afford 78% of the theoretical yield.

Example 14
Degradation tests on N,N-bis(carboxymethyl)-3-aminopropiohydroxamic acid disodium salt from Example 2

Zahn-Wellens jar test (according to EC directive 88/302/EEC, OECD 302 B, ISO 9888): Degree of DOC elimination after 17 days 86% (control substance ethylene glycol: DOC 98%)

Modified Sturm test (according to 84/449/EEC, OECD 301 B, ISO 9439): degree of DOC elimination after 35 days 100%, $CO_2$ evolution 72% of theory Use properties The substance from Example 1 was tested in its function as co-builder (incrustation inhibitor) as textile detergent additive. For this purpose, it was incorporated into a detergent formulation A of the following composition:

| | |
|---|---|
| 6.25 parts by weight | of sodium dodecylbenzenesulfonate |
| 4.70 parts by weight | of a $C_{13}/C_{15}$ oxo alcohol reacted with 7 mol of ethylene oxide |
| 1.25 parts by weight | of magnesium silicate |
| 10.00 parts by weight | of anhydrous sodium carbonate |
| 6.00 parts by weight | of sodium metasilicate tetrahydrate |
| 20.00 parts by weight | of sodium perborate tetrahydrate |
| 6.75 parts by weight | of anhydrous sodium sulfate |
| 2.80 parts byweight | of soap |
| 0.60 parts by weight | of sodium carboxymethylcellulose |
| 30.00 parts by weight | of zeolite A |
| 5.00 parts by weight | of N,N-bis(carboxymethyl)-3-aminopropiohydroxamic acid monosodium salt from Example 1 |
| Remainder to 100 parts by weight | of water |

Test cotton fabric was washed with detergent formulation A. After the washing process, the ash content of the fabric was determined by ashing 5 g of the test fabric at 700° C. for 2 hours.

The effect (E) of the detergent additive in formulation A is stated in percent activity, where 0% effect corresponds to the ash content without incrustation inhibitor, ie. without detergent additive. (A without) and 100% effect corresponds to the ash content of the fabric before washing (A zero).

The effect E of the additive is calculated from the determined ash contents (A additive) as follows:

$$E = \left(1 - \frac{(A\ additive) - (A\ zero)}{(A\ without) - (A\ zero)}\right) \times 100[\%]$$

The following washing conditions were chosen:

| Machine: | Atlas Launder-O-meter |
|---|---|
| Number of wash cycles: | 15 |
| Wash liquor: | 250 g |
| Water hardness: | 4 mmol per liter (Ca:Mg = 4:1) |
| Washing time: | 30 min at 60° C. (including heating time) |
| Liquor ratio: | 1:12.5 |
| Test fabric: | cotton cheesecloth |

The ash content of the cotton fabric before washing (A zero) was 0.04% by weight, and the maximum ash content without incrustation inhibitor (A without) was 6.91% by weight. The ash content found with the substance from Example 1 was 1.02% by weight, which corresponds to an effect E of 85.7% according to the above equation.

A comparative test carried out similarly in the same wash series using the same amount of trisodiumcitrate as prior art incrustation inhibitor alone without hydroxamic acids according to the invention afforded an effect E of 38.8%.

Similar incrustation determinations with tartarohydroxic acid led to an experimentally measured effect E of 49.5% (with an ash content without incrustation inhibitor of 4.5% by weight).

When a mixture of hydroxamic acid from Example 1 and trisodium citrate was used it was possible to increase further the incrustation-inhibiting effect because of the synergistic effect present. Incrustation determinations on use of a corresponding mixture in the ratio 1:1 by weight with a concentration of 1.6% by weight in each case of hydroxamic acid and trisodium citrate in a detergent formulation similar to A yielded an experimentally measured effect E of 54.4%, whereas the effect E calculated as the total for the two individual components was only 47% (8.6% for trisodium citrate +38.4% for the hydroxamic acid).

We claim:

1. A washing or cleaning method comprising washing a substrate with a detergent or cleaner containing a builder selected from the group consisting of N,N-bis(carboxymethyl)-3-aminopropiohydroxamic acids and their ethers of the formula IIIa

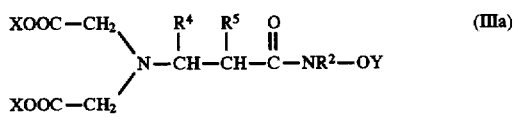

where $R^4$ is hydrogen, methyl or ethyl, $R^5$ is hydrogen, methyl, ethyl or hydroxyl;

$R^2$ is hydrogen or $C_1$–$C_{18}$-alkyl

X is hydrogen, alkali metal, ammonium or substituted ammonium, and

Y is hydrogen, alkali metal, ammonium, substituted ammonium or $C_1$–$C_{18}$-alkyl.

2. A hydroxamic acid or hydroxamic acid ether of the formula IV

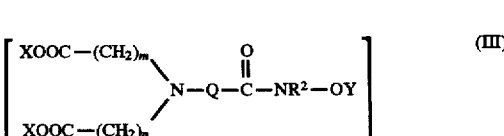

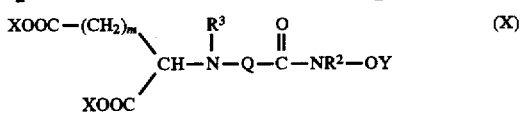

where $R^2$ is hydrogen or $C_1$–$C_{18}$-alkyl, $R^3$ is hydrogen or a group of the formula —Q—CO—$NR^2$—OY Q is a $C_1$–$C_8$-alkylene group which can additionally carry up to 8 hydroxyl groups, m is 1 or 2, and X is hydrogen, alkali metal, ammonium or substituted ammonium, and Y is hydrogen, alkali metal, ammonium, substituted ammonium or $C_1$–$C_{18}$-alkyl.

3. A process for preparing an N,N-bis(carboxymethyl)-3-aminopropiohydroxamic acid or its ether of the formula IIIa

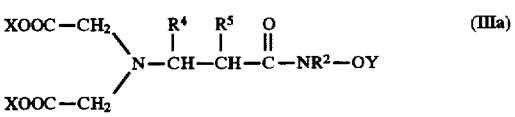

where $R^4$ is hydrogen, methyl or ethyl, $R^5$ is hydrogen, methyl, ethyl or hydroxyl, $R^2$ is hydrogen or $C_1$–$C_{18}$-alkyl, X is hydrogen, alkali metal, ammonium or substituted ammonium, and Y is hydrogen, alkali metal, ammonium, substituted ammonium or $C_1$–$C_{18}$-alkyl, which comprises reacting iminodiacetic acid of the formula VI

with an α,β-unsaturated carboxylic ester of the formula VII

or with an α,β-unsaturated carboxamide of the formula VIII

to give a N,N-bis(carboxymethyl)-3-aminopropionic ester of the formula IX

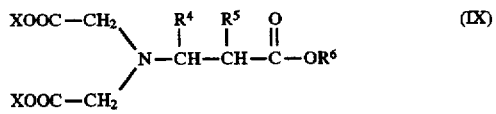

or a N,N-bis(carboxymethyl)-3-aminopropionamide of the formula X

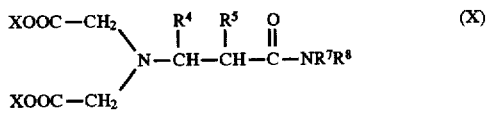

and subsequently reacting (IX) or (X) with a hydroxylamine or a hydroxylamine $C_1$–$C_{18}$-alkyl ether to give the acid or ether IIIa which is optionally converted into the salt form by treatment with bases from which X and Y are derived, with the variables $R^6$ being $C_1$–$C_4$-alkyl, and $R^7$ and $R^8$ being hydrogen or $C_1$–$C_4$-alkyl.

4. A mixture of

A) N,N-bis(carboxymethyl)-3-aminopropiohydroxamic acids or their ethers of the general formula IIIa

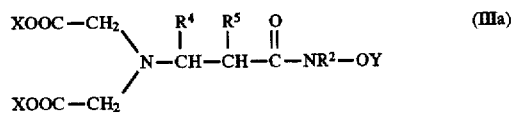

where $R^4$ is hydrogen, methyl or ethyl, $R^5$ is hydrogen, methyl, ethyl or hydroxyl, $R^2$ is hydrogen or $C_1$–$C_{18}$-alkyl, X is hydrogen, alkali metal, ammonium or substituted ammonium, and Y is hydrogen, alkali metal, ammonium, substituted ammonium or $C_1$–$C_{18}$-alkyl, and B) alkali metal salts of citric acid in the A:B ratio by weight of from 20:1 to 1:20.

* * * * *